(12) United States Patent
Sanders (10) Patent No.: US 9,933,335 B2
(45) Date of Patent: Apr. 3, 2018

(54) COMBUSTION GAS SENSOR ASSEMBLY FOR ENGINE CONTROL

(71) Applicant: Wisconsin Alumni Research Foundation, Madison, WI (US)

(72) Inventor: Scott Thomas Sanders, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 25 days.

(21) Appl. No.: 15/185,615

(22) Filed: Jun. 17, 2016

(65) Prior Publication Data

US 2017/0363513 A1 Dec. 21, 2017

(51) Int. Cl.
| | | |
|---|---|---|
| *G01M 15/10* | (2006.01) | |
| *G01N 21/15* | (2006.01) | |
| *F02D 41/14* | (2006.01) | |
| *G01N 21/3504* | (2014.01) | |

(52) U.S. Cl.
CPC ....... *G01M 15/108* (2013.01); *F02D 41/1451* (2013.01); *G01N 21/15* (2013.01); *G01N 21/3504* (2013.01); *G01N 2021/151* (2013.01); *G01N 2201/06113* (2013.01)

(58) Field of Classification Search
CPC .... G01F 1/74; G01N 21/314; G01N 21/3554; G01N 21/8507; G01N 2021/3137; G01N 2021/3166; G01N 2021/3177; G01N 2021/3188
See application file for complete search history.

(56) References Cited

U.S. PATENT DOCUMENTS

| | | | | |
|---|---|---|---|---|
| 3,861,855 A | * | 1/1975 | Seider | F23N 5/08 236/15 E |
| 4,583,859 A | * | 4/1986 | Hall, II | B01D 46/46 250/236 |
| 5,009,064 A | * | 4/1991 | Grob | G01N 21/534 60/276 |
| 5,195,356 A | * | 3/1993 | Stavinoha | G01N 21/274 356/246 |
| 5,200,629 A | * | 4/1993 | Kaiblinger | B01D 53/56 250/575 |
| 5,205,265 A | * | 4/1993 | Kashiyama | F02D 21/08 123/568.12 |
| 5,403,036 A | * | 4/1995 | Zakula | B60R 21/2644 102/202.5 |
| 5,424,842 A | * | 6/1995 | Poorman | G01N 21/15 356/438 |
| 5,592,296 A | | 1/1997 | Pye | |

(Continued)

FOREIGN PATENT DOCUMENTS

WO  2016044730 A1  3/2016

OTHER PUBLICATIONS

International Search Report for App No. PCT/US2017/031274, dated Jul. 25, 2017.

*Primary Examiner* — Sang Nguyen
(74) *Attorney, Agent, or Firm* — Boyle Fredrickson, S.C.

(57) ABSTRACT

An optical sensor for sensing combustion products avoids fouling and damage to optical components by using a "windowless" design in which an air curtain through an orifice provides a constantly refreshing transparent shield protecting the optical components from corrosive combustion gases and resisting the accumulation of particulates that might otherwise foul a static window.

17 Claims, 5 Drawing Sheets

(56) References Cited

U.S. PATENT DOCUMENTS

| | | | | |
|---|---|---|---|---|
| 5,670,074 | A * | 9/1997 | Kass | F23N 5/242 |
| | | | | 219/481 |
| 5,760,911 | A * | 6/1998 | Santschi | G01N 21/534 |
| | | | | 356/438 |
| 7,319,524 | B2 * | 1/2008 | Friedrichs | G01N 21/15 |
| | | | | 356/435 |
| 7,834,312 | B2 * | 11/2010 | Lievois | G01F 1/74 |
| | | | | 250/269.1 |
| 2006/0256330 | A1 | 11/2006 | Leipertz | |
| 2009/0229250 | A1 | 9/2009 | Yamakage et al. | |
| 2012/0239308 | A1 | 9/2012 | Miller et al. | |
| 2013/0080034 | A1 * | 3/2013 | Chi | F02D 41/0065 |
| | | | | 701/108 |
| 2016/0003736 | A1 | 1/2016 | Gigler et al. | |

* cited by examiner

COMBUSTION GAS SENSOR ASSEMBLY FOR ENGINE CONTROL

STATEMENT REGARDING FEDERALLY SPONSORED RESEARCH OR DEVELOPMENT

--

CROSS REFERENCE TO RELATED APPLICATION

--

BACKGROUND OF THE INVENTION

The present invention relates to combustion gas sensors and in particular to an optical sensor adapted for continuous engine exhaust monitoring.

Accurate, real-time information about the combustion gases and particulates produced by engines is increasingly important in the efficient control of combustion engines such as automotive gasoline engines but also including other mobile and stationary engines such as gas turbine engines. This information can be obtained by spectrographic analysis of combustion products using optical sensors that measure the absorption of light in different frequency bands as the light passes through combustion gases.

While such spectrographic sensors are routinely used in experimental environments, practical use for engine control requires a highly reliable sensor that can operate with minimal maintenance over a long period of time. One significant obstacle to long-term use of such sensors is damage to sensitive optical elements caused by the combustion gases and particulates that can accumulate on the protective optical window of the optical components reducing light transmission and/or creating erroneous readings. One approach to minimizing such fouling and damage is the use of an air curtain that flushes air across an optical window, for example, as described in U.S. Pat. No. 5,592,296 incorporated by reference. In an alternative design taught by U.S. Pat. No. 4,583,859, also incorporated by reference, clean air is flushed along the optical path of the sensor to provide an "air shield".

A disadvantage to each of these techniques is need for an ample supply of fresh air normally obtained by filtration using filters that must be frequently be cleaned and changed.

SUMMARY OF THE INVENTION

The present invention provides an optical assembly that resists damage and fouling of the optical sensors through the use of air flow through an extremely small opening into the combustion conduit (less than a millimeter in diameter and typically on the order of 80 microns). This small opening is possible through the use of a light emitter with high spatial coherence (e.g. a laser or super luminescent source) and advantageously resists fouling by permitting higher air flow velocities for a given pump power and filter consumption. In addition, the extremely small hole size can block insect entry, moisture, and dust accumulation.

Specifically then, at least one embodiment of the invention provides an engine sensor having a conduit communicating with a combustion engine to receive combustion gases channeled by walls of the conduit, the walls including at least one orifice having an area of less than one square millimeter therethrough. A high spatial coherence light emitter with a predetermined spectral content is positioned to direct light through the at least one orifice through combustion gases within the conduit and a light receiver is positioned to detect the light after passage through the combustion gases and the at least one orifice to produce an electrical signal indicating spectral absorption of the light by the combustion gases in at least two frequencies A source of air provides a pressure greater than a pressure within the conduit and communicates with the at least one orifice to provide a substantially continuous shielding airflow through the at least one orifice during operation of the combustion engine to prevent passage of combustion gases into the orifices and a buildup of particles from the combustion gas on the at least one orifice.

It is thus a feature of at least one embodiment of the invention to provide accurate optical sensing for long-term combustion engine monitoring with reduced power usage and reduced degradation of the sensor.

The high spatial coherence light emitter may be selected from the group consisting of a laser light emitter and a super luminescent light emitter.

It is thus a feature of at least one embodiment of the invention to permit the use of small orifice sizes through the use of light emitters that can be readily collimated into small area beams.

The light emitter may include a lens receiving light from the light emitter and providing a focal point of the light located in the at least one orifice or a light guide leading to the at least one orifice.

It is thus a feature of at least one embodiment of the invention to maximize light transmission through a small orifice by approximately setting the focal length of the lens to the orifice center.

The total area of the orifice may be selected so that pressurized air introduced into the conduit through the orifice has a mass flow rate of less than 100 parts per million of the total mass flow rate of the gas passing through the conduit.

It is thus a feature of at least one embodiment of the invention to provide a system that does not adversely affect measurement of the combustion gases.

Each orifice may have a diameter of less than one square millimeter.

It is thus a feature of at least one embodiment of the invention to provide sufficient air velocity for shielding while reducing air pumping costs.

The light emitter and light receiver may have transparent optical elements through which the light passes and the transparent optical elements may be displaced away from the orifice to be protected from contact with the combustion gases by a shielding effect of the pressurized air.

It is thus a feature of at least one embodiment of the invention to not only prevent blockage of the orifice but to shield the optical elements from corrosive gases.

A particulate filter may be positioned to filter particulates from the source of pressurized air that could block the orifice before the pressurized air is received by the at least one orifice.

It is thus a feature of at least one embodiment of the invention to permit the use of available ambient air even if contaminated with exhaust or other particulates.

A heater may be positioned for heating the air that provided to the at least one orifice.

It is thus a feature of at least one embodiment of the invention to prevent moisture buildup or frost from interfering with the operation of the sensor when a small orifice size is used.

The engine sensor may further include an electronic computer receiving the electrical signal to provide a control signal to the combustion engine controlling the combustion engine to change the combustion gases.

It is thus a feature of at least one embodiment of the invention to provide sophisticated engine control possible with optical sensing.

The source of pressurized air may be controlled by an electronic circuit to vary the air pressure.

It is thus a feature of at least one embodiment of the invention to provide both continuous protection and burst particulate removal.

These particular objects and advantages may apply to only some embodiments falling within the claims and thus do not define the scope of the invention.

DETAILED DESCRIPTION OF THE PREFERRED EMBODIMENT

Figure 1:
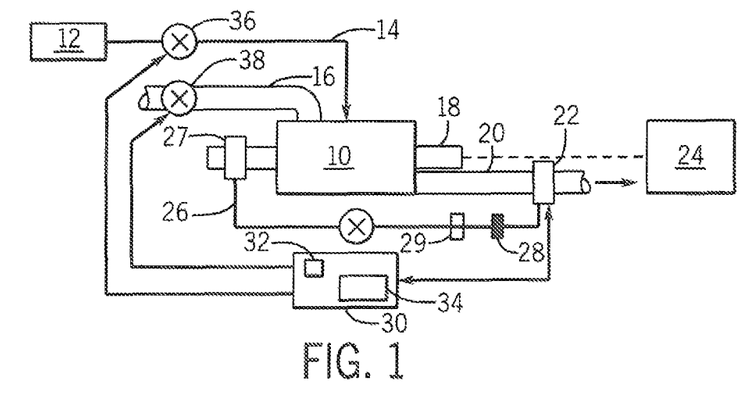
FIG. 1 is a simplified block diagram of a combustion engine receiving air and fuel to provide mechanical power through an output shaft and showing a sensor assembly of the present invention measuring exhaust gases from the engine and receiving compressed air from the engine.

Referring now to FIG. 1, a combustion engine 10, including but not limited to a gas turbine, diesel or gasoline engine, may receive fuel 12 over fuel line 14 and air through an air intake 16 to provide mechanical energy through a driveshaft 18 using energy released from the combustion of the air and fuel. The driveshaft 18 will typically drive a load 24, for example, an electrical generator, pump, vehicle or the like.

Combustion products from the combustion engine 10 are conducted through an exhaust pipe 20 that passes through a sensor system 22 of the present invention. These combustion products are then received by pollution control measures (not shown) and discharged into the atmosphere. Alternatively, the pollution control measures could be located before the sensor system, for example, when the sensor system is monitoring such control measures.

A small portion of the power from the combustion engine 10 may be used to provide a source of pressurized air over air line 26, for example, using a compressor 27 driven directly or indirectly by the driveshaft 18. The invention also contemplates that a separate external air source may be used as will be discussed below.

Pressurized air passing through air line 26 may be received by a heater 29 and then by particulate filter 28 and is then provided to the sensor system 22 for use as will be described below.

Data from the sensor system 22 may be provided to an engine controller 30, the latter, for example, including a processor 32 and a memory 34 holding a stored program for engine control. Based on the data from the sensor system 22 which may indicate concentrations of different gaseous species, particulates, and the like, the engine controller 30 may control the engine 10 for improved performance or may monitor the engine 10, for example, with respect to maintenance. This control may be implemented by a variety of known techniques including controlling the fuel 12 passing through the fuel line 14 by valve 36 and/or controlling air passing through the air intake 16 by means of valve 38 or by other engine control inputs, for example, camshaft timing, piston displacement adjustments, or in the case of an ignition engine, ignition timing and the like.

Figure 2:
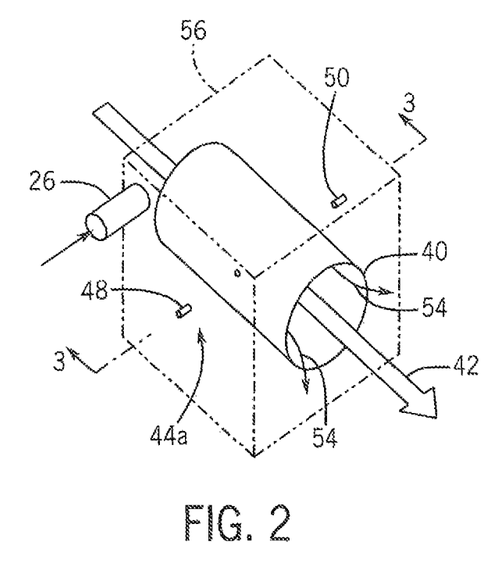
FIG. 2 is a phantom view of the sensor assembly of FIG. 1 providing an enclosed pressurized housing fitting about an exhaust conduit.
Figure 3:
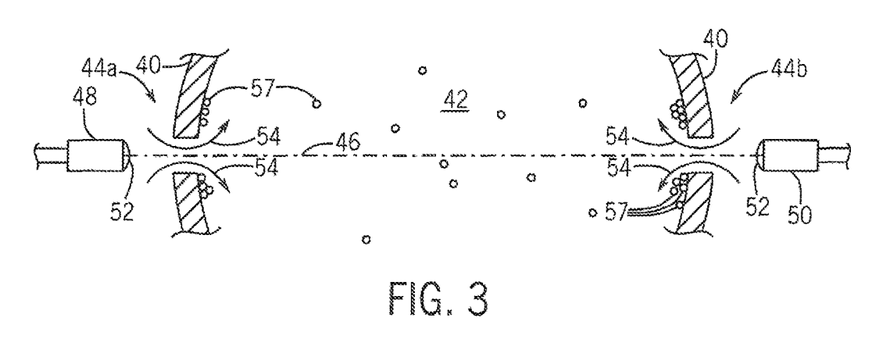
FIG. 3 is a fragmentary cross-section along line 3-3 of FIG. 2 showing the optical path employed by the sensor through the exhaust conduit in one embodiment and the flow of air through orifice is aligned with that optical path, the latter providing an air curtain protecting the optics and preserving a clear optical path through the exhaust conduit.
Figure 4:
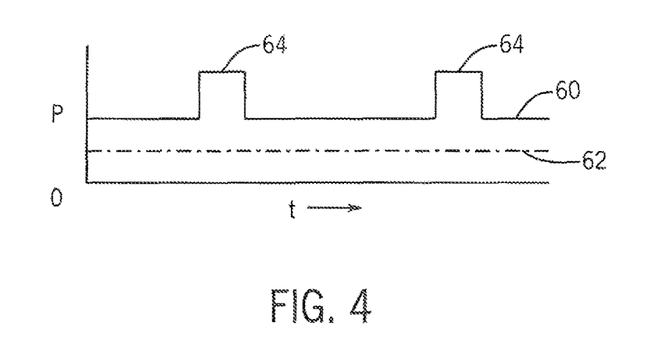
FIG. 4 is a graph of a combination steady-state and air pulse flow that can be used in the present invention.

Referring now to FIGS. 2 and 3, the sensor system 22 may provide for a tubular conduit 40 receiving combustion gases 42 from the exhaust pipe 20. Diametrically opposed orifices 44a and 44b may be cut through the walls of the conduit 40 to define a generally straight-line optical path 46 therebetween.

Positioned in opposition on either side of the conduit 40 and aligned with the optical path 46 is a light emitter 48 and a light receiver 50 that may respectively transmit and receive multispectral light to make spectrographic measurements of the gas in the conduit 40. The light emitter 48 is such as to provide a high spatial coherence in the manner of a laser or super luminescent light emitter so as to provide focused power through an extremely small orifice thereby compensating for the small orifice area.

One or both of the light emitter 48 and light receiver 50 may have optical elements 52 such as lenses, windows, collimators, or the like through which light is transmitted or received and may provide an interface to the external environment. These optical elements 52 will be displaced away from the orifices 44a and 44b to allow airflow 54 past the optical elements 52 through the orifices 44a and 44b into the internal volume of the conduit 40.

To provide this airflow 54, the conduit 40 may be surrounded by a secondary chamber 56 receiving air line 26 after filtration by filter 28 to provide an enclosed and pressurized source of particulate-free air at a higher pressure than the peak pressure found in the conduit 40 to distribute this air to the orifices 44a and 44b supporting a substantially continuous airflow 54 through the orifices 44a and 44b. The airflow 54 provides the functions of shielding the optical elements 52 from corrosive pitting by the combustion gases in the manner of an air curtain and further prevents the accumulation of particulates 57 within or over orifices 44a and 44b that might block the optical path 46. Because the airflow 54 is substantially transparent, it creates an effective constantly regenerating window resistant to fouling.

The inventor has determined that the beneficial properties of the airflow 54 in maintaining unobstructed optical path 46 can be obtained without affecting the validity of the measurement of the combustion gases 42 by using small diameter orifices 44a and 44b and a small diameter light beam, each which may be, in one example, 80 microns in diameter. More generally the total area of each of the orifices 44a and 44b may be less than one square millimeter or preferably 10,000 square microns. In all cases, the mass airflow 54 may be generally less than 1000 parts per million and preferably less than 10 parts per million of the total mass of the combustion gases 42 while still providing suitable protective function.

Referring now to FIGS. 1 and 2, in one embodiment the pressure 60 of the air in the outer chamber 56 will be maintained above the pressure 62 of the combustion gases in the conduit 40 on a substantially continuous basis at any time when the engine 10 is operating. Ideally, this pressure 62 rises slightly ahead of the pressure rise in the conduit 40 and may continue at an elevated pressure for a short period of time (for example, through the use of an accumulator) after operation of engine 10 ceases. In one embodiment the pressure is periodically substantially increased in pressure bursts 64 of less than the second, for example, peak pressure, and the pressure bursts 64 have twice a pressure difference between the peak pressure of the pressure bursts 64 and the conduit pressure 62 when compared to the difference between the steady-state pressure 60 and the conduit pressure 62. This burst operation effects a flexible trade-off between energy use, combustion gas dilution, and cleaning effectiveness. During the pressure bursts 64 spectrographic measurement may be temporarily ceased.

Figure 5:
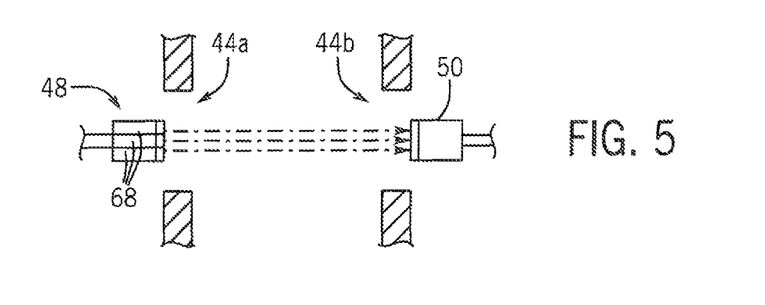
FIGS. 5 and 6 are simplified block diagrams of different implementations of the light sensor and light emitter used in the optical sensing assembly for transmission measurements.

Referring now to FIG. 5, in one embodiment the light emitter 48 may provide for multiple narrowband light transmitters 68 that may be sequentially activated to individually transmit light to a broadband light receiver 50. The sequential activation of the narrowband light transmitters 68 allows the light receiver 50 to record the separate absorption signals for each of the frequencies of the narrowband light transmitters 68. These absorption measurements may compare the amplitude of the received signal to a baseline signal, for example, obtained when there is no combustion gas within the conduit 40, to deduce an absorption value.

Figure 6:
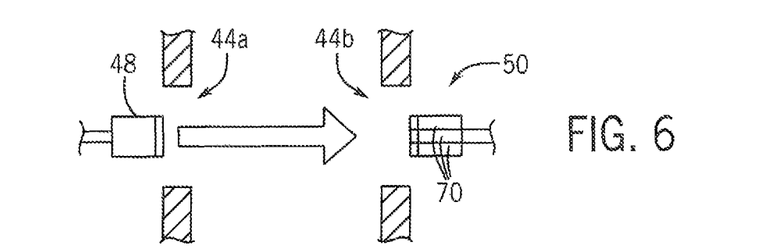

Referring to FIG. 6, alternatively, the light emitter 48 may be a broadband or multispectral light transmitter having a bandwidth spanning the entire intended spectrum of the spectrographic measurement (typically including infrared frequencies) and the light receiver 50 may provide for multiple narrowband light sensors 70, for example, using appropriate light filters or the like to provide frequency-selective sensitivity. Here each of the narrowband light sensors 70 may provide a separate attenuation signal to the engine controller.

Figure 7:
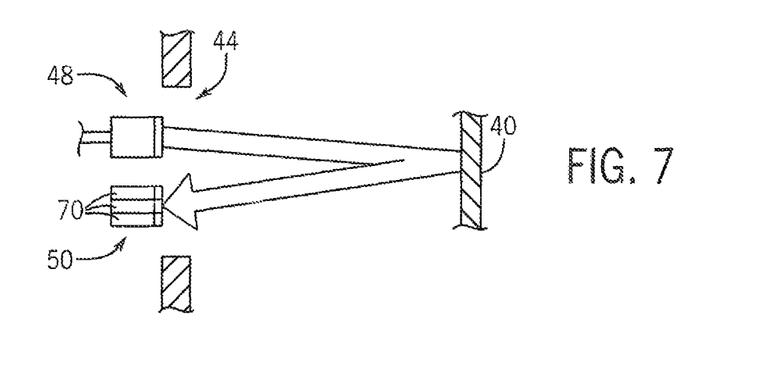
FIGS. 7 and 8 are figures similar to those of FIGS. 5 and 6 showing different implementations of the light sensor and light emitter used in the optical sensing assembly for reflection measurements.
Figure 8:
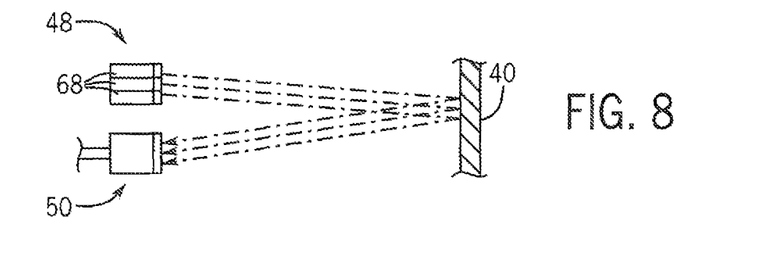

Referring now to FIG. 7, the dual orifices 44a and 44b shown in FIG. 3 may be replaced with a single orifice 44 and the light may be transmitted through the single orifice 44 into the conduit 40 to scatter from an inner wall of the conduit 40 to return out of the same orifice 44. In one embodiment similar to that of FIG. 6, the light emitter 48 may be a single broadband light transmitter and the light receiver 50 may have multiple narrowband light sensors 70. Alternatively as shown in FIG. 8, light emitter 48 as discussed with respect to FIG. 5, may include multiple narrowband light transmitters 68 sequentially operated and the light receiver 50 may be a broadband light receiver whose signal is demodulated by the engine controller 30 to obtain separate spectral measurements. The invention anticipates that at least two and more typically three different spectral bands will be measured.

Figure 9:
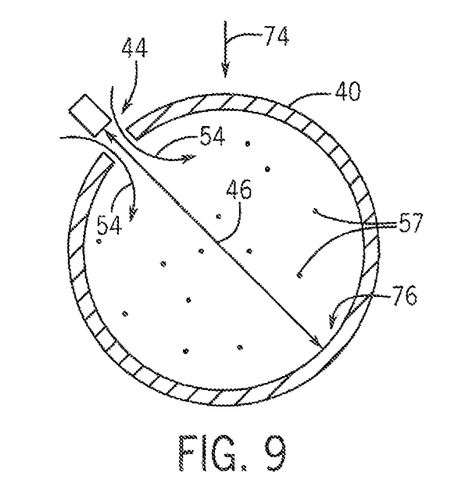
FIG. 9 is a cross-section similar to that of FIG. 3 showing orientation of the optical path in reflection measurement elevating the orifice to further resist fouling.

Referring to FIG. 9, using the backscattering system of FIGS. 7 and 8, the optical path 46 may be positioned, for example, at an angle with respect to a vertical direction 74 (with the axis of the conduit 40 being generally horizontal) so as to elevate the orifice 44 reducing the tendency of particulates 57 from collecting thereon under the influence of gravity. In this case, the backscattering surface 76 of the interior of the conduit 40 is also removed from the lowest point in the conduit 40 so as to reduce backscattering changes that may be caused by the accumulation of material along the bottom wall of the conduit 40.

Figure 10:
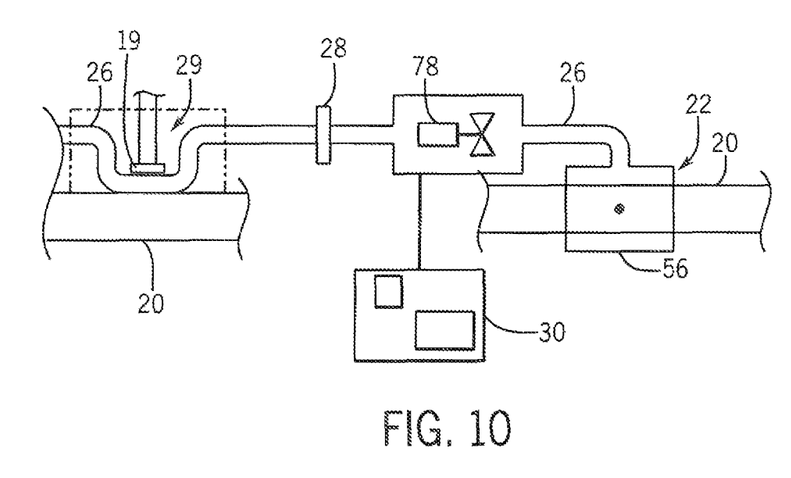
FIG. 10 is an alternative embodiment showing an electric blower used for generating the compressed air used in the air curtain of the present invention.

Referring now to FIG. 10, the source of pressurized air on air line 26 may alternatively be provided by a dedicated electrical blower or fan 78 receiving air from filter 28 and conducting it to the outer chamber 56 of the sensor system 22. This fan 78 may be controlled by the engine controller 30 in the manner described above to provide continuous operation with pulse pressure changes. The electrical power for the fan 78 may be obtained by batteries and/or a generator attached to the combustion engine 10.

The heater 29 may be positioned upstream or downstream from the fan and may incorporate one or both of an electrical resistance heater 79 communicating with the air line 26 and a heat exchanger between the air line 26 and the exhaust pipe 20 for preheating the air in the air line 26. This preheated air helps to remove moisture from the environment of the sensors and/or icing in cold weather. As such, the resistance heater 79 may be activated before the exhaust pipe 20 is fully heated to provide advanced defrosting of the sensor system.

Figure 11:
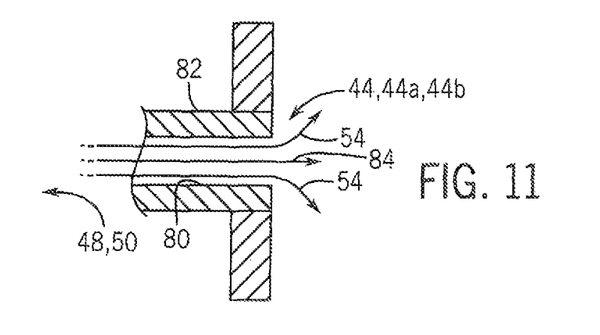
FIG. 11 is an implementation of the present invention using an internally reflective hollow light pipe.

Referring now to FIG. 11, in one embodiment, the orifices 44 (including any of the embodiments described above including orifices 44a and 44b) may be formed by a center channel 80 of a hollow light pipe 82, for example, the light pipe 82 being a metal tube with internally backscattering inner surfaces. This light pipe 82 may conduct light 84 along its inner channel via internal reflections from the light emitter 48 or to the light receiver 50 which may be thereby giving greater separation of these elements from the combustion gases 42 from inside the conduit 40 by the length of the light pipe 82. In addition the central channel of the light pipe 82 may conduct the airflow 54. Again a windowless optical interface is generated that is constantly flushed through the use of particulate free fresh air.

Figure 12:
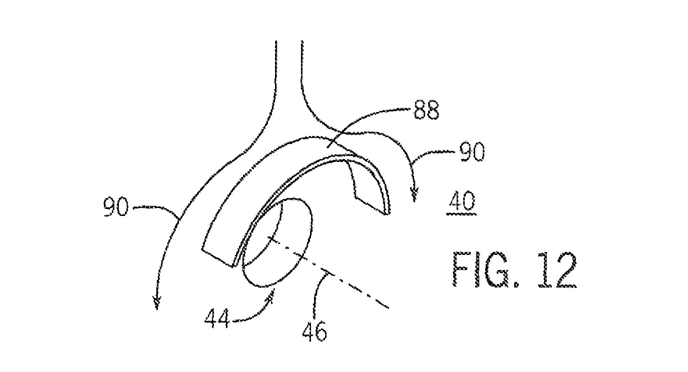
FIG. 12 is a detail of the orifice as seen within the conduit of FIG. 3 or 9 showing a moisture-diverting feature.

Referring now to FIG. 12, in one embodiment, the orifice 44 may provide for a shield 88 projecting from the inner surface of the conduit wall perpendicularly therefrom to partially surround the orifice 44 thereby diverting any condensation flow 90 caused by the force of gravity and such as may wash particulate matter into the orifice 44 around the orifice 44.

Figure 13:
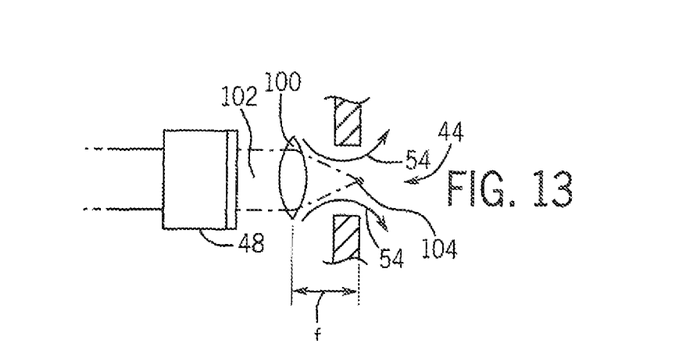
FIG. 13 is a fragmentary cross-section similar to FIG. 3 showing use of a lens system for focusing light through the small orifice.

Referring now to FIG. 13, the light emitter 48 may be associated with a lens 100 (or mirror) receiving light 102 from the light emitter 48 to focus it at a focal point 104 centered within the orifice 44 to maximize light transmission there through.

Figure 14:
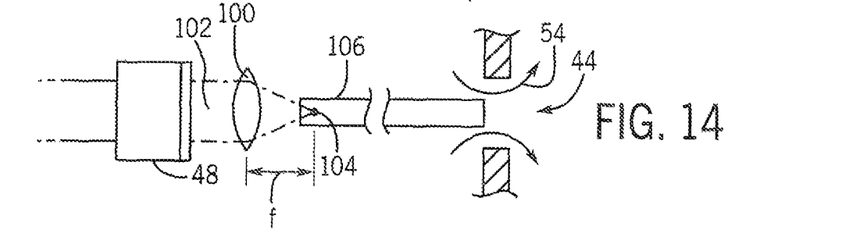
FIG. 14 is a figure similar to that of FIG. 13 showing the use of a light guide to displace the lens from the orifice with similar focusing effect.

Alternatively, as shown in FIG. 14, the lens 100 may have its focal point 104 adjusted to lie at the entrance aperture of a light guide 106 such as an optical fiber or the light pipe discussed with respect to FIG. 11. This allows the light emitter 48 to be further separated from the orifice 44 while still providing a high amount of light transmission through a small area.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller", "a circuit" and "a processor" or "the microprocessor" and "the processor," can be understood to include one or more circuits or microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network. A single microprocessor or similar computer executing different programs may provide different circuits by virtue of the programs control of current flow in hardware. Accordingly, it will be understood that the invention contemplates that the described circuits may be implemented flexibly through discrete circuitry, microcoding (firmware) and associated processing circuitry, gate arrays, and general-purpose processors executing programs including special application programs and/or operating system functions.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

The invention claimed is:

1. An engine sensor comprising:
 a conduit communicating with a combustion engine to receive combustion gases channeled by walls of the conduit, the walls including at least one orifice having an area of less than one square millimeter therethrough;
 a high spatial coherence light emitter having a predetermined spectral content positioned to direct light through the at least one orifice and through combustion gases within the conduit;
 a light receiver position to detect the light after passage through the combustion gases and the at least one orifice to produce an electrical signal indicating spectral absorption of the light by the combustion gases in at least two frequencies; and
 a source of air providing a pressure greater than a pressure within the conduit and communicating with the at least one orifice to provide a substantially continuous shielding airflow through the at least one orifice during operation of the combustion engine to prevent passage of combustion gases into the at least one orifice and a buildup of particles from the combustion gas on the at least one orifice;
 wherein the pressure of the air and a total area of the at least one orifice is selected so that air introduced into the conduit through the at least one orifice has a mass of less than 1000 parts per million of the total mass of the combustion gas passing through the conduit.

2. The engine sensor of claim 1 wherein the at least one orifice has an area of less than 10,000 square micrometers.

3. The engine sensor of claim 2 wherein the pressure of the air and a total area of the at least one orifice is selected so that pressurized air introduced into the conduit through the at least one orifice has a mass of less than 10 parts per million of the total mass of combustion gas passing through the conduit.

4. The engine sensor of claim 1 wherein the high spatial coherence light emitter is selected from the group consisting of a laser light emitter and a super luminescent light emitter.

5. The engine sensor of claim 4 wherein the light emitter includes a lens receiving light from the light emitter and providing a focal point of the light located in the at least one orifice or a light guide leading to the at least one orifice.

6. The engine sensor of claim 5 including a particulate filter positioned to filter particulates from the source of pressurized air that could block the at least one orifice before the pressurized air is received by the at least one orifice.

7. The engine sensor of claim 5 including a heater for heating the air that is provided to the at least one orifice.

8. The engine sensor of claim 1 further including an electronic computer receiving the electrical signal to provide a control signal to the combustion engine controlling the combustion engine to change the combustion gases.

9. The engine sensor of claim 1 wherein the light emitter is a broad spectrum light emitter and the light detector is a spectrally discriminating light detector discriminating among light within the broad spectrum.

10. The engine sensor of claim 1 wherein the light emitter is a set of individually activatable light emitters each producing a different narrow spectrum and the light detector is a broad spectrum light detector detecting each of the narrow spectrums of the light emitter.

11. The engine sensor of claim 1 wherein the at least one orifice is a single orifice shared by the light emitter and the light detector.

12. The engine sensor of claim 1 wherein the at least one orifice is two different orifices along a common axis adjacent to a different one of the light emitter and the light detector.

13. The engine sensor of claim 1 wherein the source of pressurized air is an electric gas pump controlled by an electronic circuit.

14. The engine sensor of claim 1 wherein the source of pressurized air is a mechanical gas pump powered by the combustion engine.

15. An engine sensor comprising:
- a conduit communicating with a combustion engine to receive combustion gases channeled by walls of the conduit, the walls including at least one orifice having an area of less than one square millimeter therethrough;
- a high spatial coherence light emitter having a predetermined spectral content positioned to direct light through the at least one orifice and through combustion gases within the conduit;
- a light receiver position to detect the light after passage through the combustion gases and the at least one orifice to produce an electrical signal indicating spectral absorption of the light by the combustion gases in at least two frequencies; and
- a source of air providing a pressure greater than a pressure within the conduit and communicating with the at least one orifice to provide a substantially continuous shielding airflow through the at least one orifice during operation of the combustion engine to prevent passage of combustion gases into the at least one orifice and a buildup of particles from the combustion gas on the at least one orifice;
- wherein the source of pressurized air is controlled by an electronic circuit to provide vary the pressure;
- wherein the second pressure provides a pressure difference from a pressure of the conduit at least twice as high as the first pressure.

16. A method of monitoring combustion gases from a combustion engine using an engine sensor having:
- a conduit communicating with a combustion engine to receive combustion gases channeled by walls of the conduit, the walls including at least one orifice having an area less than one square millimeter therethrough;
- a high spatial coherence light emitter having a predetermined spectral content positioned to direct light through the at least one orifice and through combustion gases within the conduit;
- a light receiver detecting the light after passage through the combustion gases to produce an electrical signal indicating spectral absorption of the light by the combustion gases in at least two frequencies; and
- a source of air providing a pressure greater than a pressure within the conduit and communicating with the at least one orifice to provide a shielding airflow through the orifice to prevent a buildup of particles from the combustion gas on the orifice;

the method comprising:
- (a) at a time proximate to initiation of operation of the combustion engine, providing the air to the at least one orifice to establish a continuous airflow through the at least one orifice into the conduit to provide a scavenging airflow through the orifice to prevent a buildup of particles from the combustion gas on the orifice; and
- (b) during the scavenging airflow, operating the light emitter and light receiver to detect spectral absorption of the light by the combustion gases in at least two frequencies;
- wherein the pressurized air and a total area of the at least one orifice are selected so that air introduced into the conduit through the at least one orifice is less than 1000 parts per million of the total gas passing through the conduit.

17. The method of claim 16 wherein the light emitter and light receiver have transparent optical elements through which the light passes and wherein the transparent optical elements are displaced away from the orifice to be protected from contact with the combustion gases by a shielding effect of the pressurized air.

* * * * *